US006647755B2

(12) United States Patent
Rabiner et al.

(10) Patent No.: US 6,647,755 B2
(45) Date of Patent: Nov. 18, 2003

(54) METHOD FOR MANUFACTURING SMALL DIAMETER MEDICAL DEVICES

(75) Inventors: Robert A. Rabiner, North Reading, MA (US); Bradley A. Hare, Chelmsford, MA (US); Janniah S. Prasad, Norwalk, CT (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 43 days.

(21) Appl. No.: 10/092,862

(22) Filed: Mar. 6, 2002

(65) Prior Publication Data

US 2002/0124617 A1 Sep. 12, 2002

Related U.S. Application Data

(60) Provisional application No. 60/274,037, filed on Mar. 7, 2001.

(51) Int. Cl.[7] .............................. B21C 1/28; B21C 1/18; B21C 9/00
(52) U.S. Cl. .............................. 72/291; 72/276; 72/285; 72/286
(58) Field of Search ...................... 72/41, 281, 282, 72/290, 291, 276, 274, 285, 286

(56) References Cited

U.S. PATENT DOCUMENTS

| | | | | |
|---|---|---|---|---|
| 404,319 A | * | 5/1889 | Taylor | 72/281 |
| 414,090 A | * | 10/1889 | Taylor | 72/468 |
| 1,239,451 A | | 9/1917 | Belz | |
| 1,779,478 A | | 10/1930 | Leech | |
| 2,199,602 A | * | 5/1940 | Wright | 72/276 |
| 3,763,680 A | | 10/1973 | Godfrey et al. | 72/43 |
| 3,805,787 A | | 4/1974 | Banko | 128/276 |
| 3,962,898 A | * | 6/1976 | Tillmann | 72/279 |
| 4,462,242 A | | 7/1984 | Morgenthaler | 72/467 |
| 4,870,953 A | | 10/1989 | DonMicheal et al. | 128/24 A |
| 4,872,333 A | | 10/1989 | Burnand | 72/467 |
| 4,922,902 A | | 5/1990 | Wuchinich et al. | 604/22 |
| 4,931,047 A | | 6/1990 | Broadwin et al. | 604/22 |
| 4,989,583 A | | 2/1991 | Hood | 128/24 A |
| 5,058,570 A | | 10/1991 | Idemoto et al. | 128/24 AA |
| 5,112,300 A | | 5/1992 | Ureche | 604/22 |
| 5,180,363 A | | 1/1993 | Idemoto et al. | 202/32 |
| 5,217,465 A | | 6/1993 | Steppe | 606/107 |
| 5,255,551 A | | 10/1993 | Vetter | 72/290 |
| 5,261,805 A | | 11/1993 | Gates | 425/72.1 |
| 5,325,698 A | | 7/1994 | Nagpal et al. | 72/267 |
| 5,421,338 A | | 6/1995 | Crowley et al. | 128/662.06 |
| 5,469,853 A | | 11/1995 | Law et al. | 128/662.06 |
| 5,492,001 A | | 2/1996 | Sasaki et al. | 72/359 |
| 5,527,273 A | | 6/1996 | Manna et al. | 604/22 |
| 5,676,011 A | | 10/1997 | Allison | 72/290 |

(List continued on next page.)

OTHER PUBLICATIONS

PCT International Search Report for International Application No. PCT/US02/07135 dated Jun. 5, 2002.

*Primary Examiner*—Daniel C. Crane
(74) *Attorney, Agent, or Firm*—Palmer & Dodge, LLP; Richard B. Smith; David J. Dykeman

(57) ABSTRACT

An apparatus and method for manufacturing small diameter ultrasonic probes capable of vibrating in a transverse mode that can be used in ultrasonic tissue ablation. The apparatus includes a die, a style puller which is used to engage a functional end of the medical device, and a die room puller which is used to draw the medical device through the die. The die includes a bell-shaped lead-in on a front side of the die and a bell-shaped lead-in on a back side of the die allowing for reversal of the direction of the draw. The method of manufacturing includes heat treating a large diameter medical device, drawing the large diameter device through a die and reversing the draw of the medical device through the die to provide a medical device having a varying diameter along a length of the device. The method is repeated until a final diameter is reached.

39 Claims, 2 Drawing Sheets

U.S. PATENT DOCUMENTS

| | | | |
|---|---|---|---|
| 5,687,474 A | 11/1997 | Hamzehdoost et al. | 29/832 |
| 5,704,787 A | 1/1998 | Hickok et al. | 433/166 |
| 5,758,420 A * | 6/1998 | Schmidt et al. | 29/896.9 |
| 5,765,418 A * | 6/1998 | Rosenberg | 72/47 |
| 5,803,083 A | 9/1998 | Buck et al. | 128/660.03 |
| 5,820,300 A * | 10/1998 | Sonoda et al. | 405/188 |
| 5,840,151 A | 11/1998 | Munsch | 156/380.2 |
| 5,981,444 A * | 11/1999 | Sawada et al. | 505/433 |
| 5,993,408 A | 11/1999 | Zaleski | 604/22 |
| 6,062,059 A | 5/2000 | Feldcamp | 72/271 |
| 6,107,161 A | 8/2000 | Kitaguro et al. | 438/462 |
| 6,124,150 A | 9/2000 | Corisis | 438/123 |
| 6,124,546 A | 9/2000 | Hayward et al. | 174/52.2 |
| 6,124,634 A | 9/2000 | Akram et al. | 257/698 |
| 6,307,156 B1 * | 10/2001 | Avellanet | 174/128.1 |

* cited by examiner

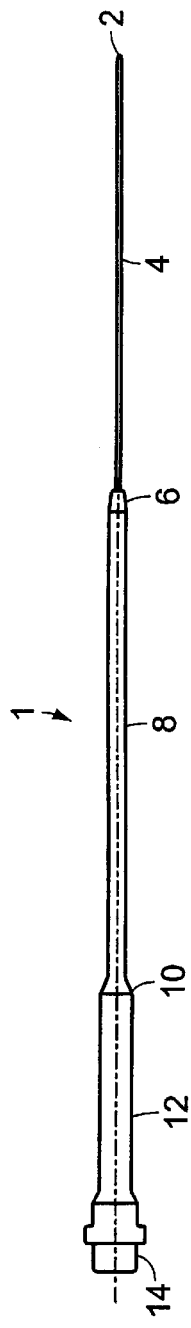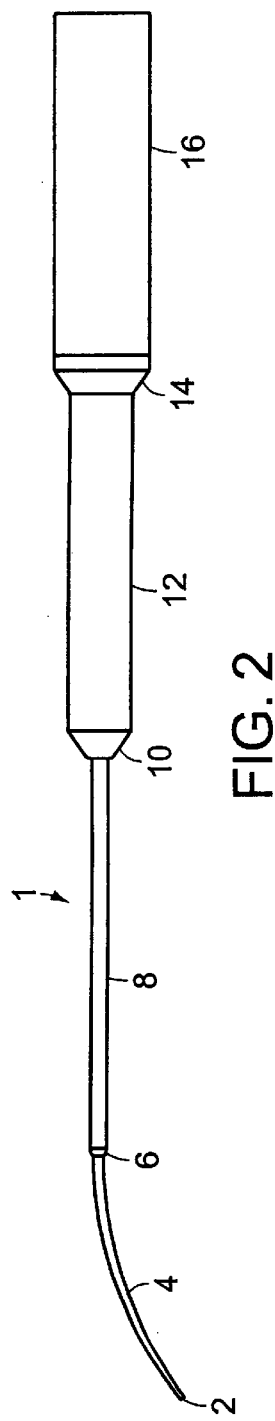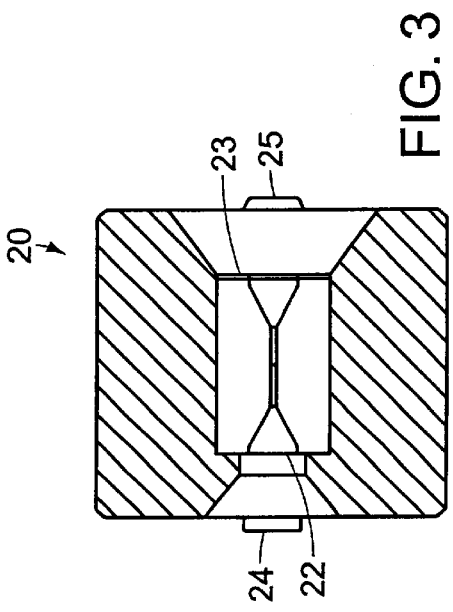

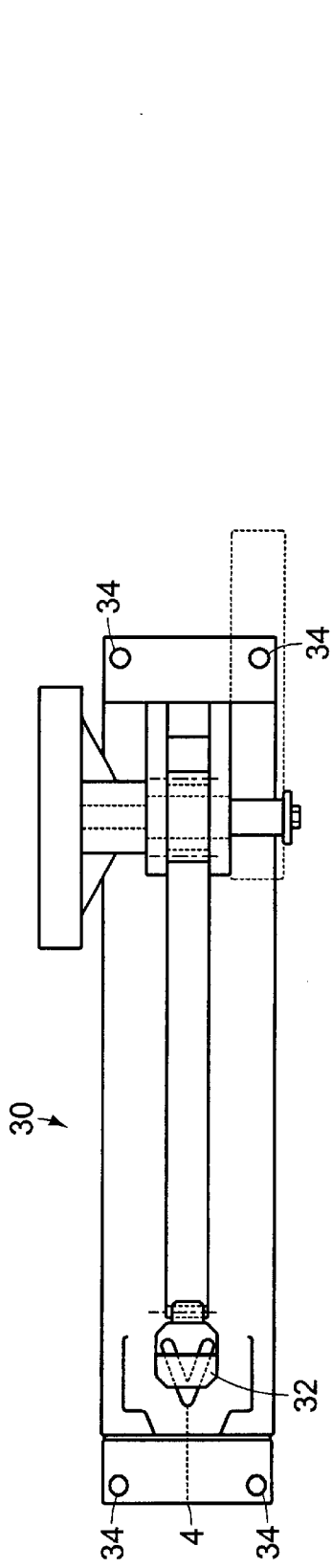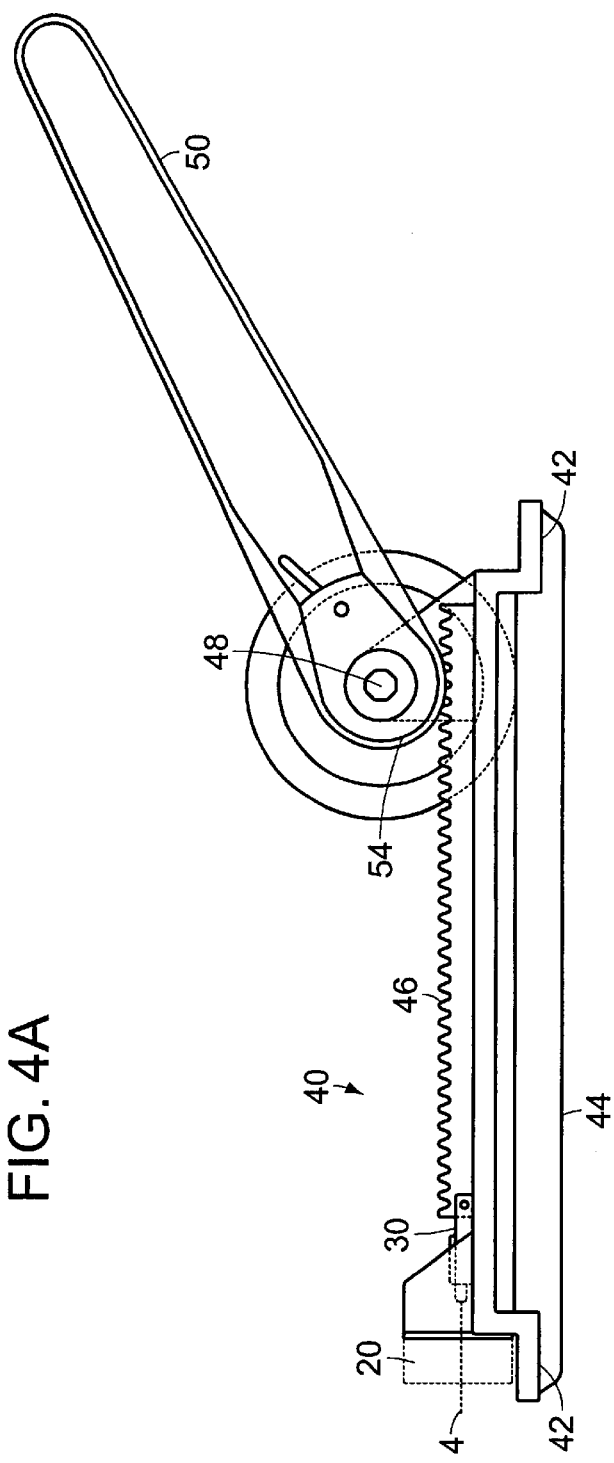
FIG. 4A
FIG. 4B

METHOD FOR MANUFACTURING SMALL DIAMETER MEDICAL DEVICES

RELATED APPLICATIONS

This application claims priority from U.S. Provisional Patent Application Serial No. 60/274,037, entitled "Apparatus and Method for Manufacturing Small Diameter Medical Devices", filed on Mar. 7, 2001 by inventors Robert A. Rabiner, Bradley A. Hare, and Janniah S. Prasad, the entirety of which is hereby incorporated by reference.

FIELD OF THE INVENTION

The present invention relates generally to the manufacture of small diameter medical devices. More particularly, the present invention is an apparatus and method for manufacturing small diameter ultrasonic probes capable of vibrating in a transverse mode that can be used in ultrasonic medical devices for tissue ablation.

BACKGROUND OF THE INVENTION

Ultrasonic probes are devices which use ultrasonic energy to fragment body tissue or debris (see, e.g., U.S. Pat. No. 5,112,300; U.S. Pat. No. 5,180,363; U.S. Pat. No. 4,989,583; U.S. Pat. No. 4,931,047; U.S. Pat. No. 4,922,902; and U.S. Pat. No. 3,805,787) and have been used in many surgical procedures. The ultrasonic energy produced by an ultrasonic probe is in the form of very intense, high frequency sound vibrations that result in powerful chemical and physical reactions in the water molecules within a body tissue or surrounding fluids in proximity to the probe. These reactions ultimately result in a process called "cavitation," which can be thought of as a form of cold (i.e., non-thermal) boiling of the water in the body tissue, such that microscopic bubbles are rapidly created and destroyed in the water creating cavities in their wake. As surrounding water molecules rush in to fill the cavity created by collapsed bubbles, they collide with each other with great force. Cavitation results in shock waves running outward from the collapsed bubbles which can wear away or destroy material such as surrounding tissue or debris in the vicinity of the ultrasonic probe. Medical applications for ultrasonic probes include, for example, treatment of cancer, tissue remodeling, liposuction, tissue biopsy, and removal of vascular occlusions.

A drawback of existing ultrasonic medical probes is that they typically remove tissue slowly in comparison to instruments that excise tissue by mechanical cutting, electrocautery, or cryoexcision methods. Part of the reason for the slow removal of tissue is that most existing ultrasonic devices rely on a longitudinal vibration of the tip of the probe for their tissue-disrupting effects. Because the tip of the probe is vibrated in a direction in line with the longitudinal axis of the probe, a tissue-destroying effect is only generated at the tip of the probe. The concentration of energy at the probe tip results in the generation of heat at the probe tip, which can create tissue necrosis, thereby complicating the surgical procedure and potentially compromising the recovery of the patient.

Complications such as these may be avoided by an ultrasonic device which includes an ultrasonic probe whose vibrations are restricted to occur exclusively in a transverse direction to the probe axis (perpendicular). By eliminating the axial motion of the probe and allowing transverse vibrations only, fragmentation of large areas of tissue spanning the entire length of the probe is possible due to generation of multiple cavitational nodes along the probe length perpendicular to the probe axis. Since substantially larger affected areas within an occluded blood vessel, organ, graft or port can be denuded of the occluding tissue or debris in a short time, actual treatment time using the transverse mode ultrasonic medical device is greatly reduced as compared to methods using probes that primarily utilize longitudinal vibration (along probe axis) for tissue or debris ablation. Another advantage to ultrasonic devices which operate in a transverse mode is their ability to rapidly remove tissue or debris from large areas within cylindrical or tubular surfaces which is not possible by devices that rely on the longitudinal vibrating probe tip for effecting tissue fragmentation.

Ultrasonic probes currently known in the art are generally made by a process of machining to achieve a diameter of approximately 0.020 inches, or greater, at the functional end of the probe. Dies are commonly known in the art and are used in the machining process (see, e.g., U.S. Pat. No. 5,840,151; U.S. Pat. No. 5,325,698; U.S. Pat. No. 5,261,805; and U.S. Pat. No. 6,062,059). Although it is possible to induce transverse vibrations at an ultrasonic probe diameter of 0.020 inches (see, e.g., U.S. Pat. No. 5,803,083; U.S. Pat. No. 5,058,570; U.S. Pat. No. 5,469,853; and U.S. Pat. No. 5,421,338), probe diameters less than 0.020 inches are crucial for the generation of sufficient cavitational energy via transverse vibration needed for the treatment of tissue. Since probes vibrating exclusively in a transverse mode must rely almost entirely on generation of sufficient cavitational energy to cause tissue ablation, the diameter of the distal segment of the probe and the probe tip have to be smaller than conventional prior art probes that are only capable of longitudinal vibration. The manufacturing methods for conventional, longitudinally vibrating ultrasonic probes disclosed in the art typically involve machining techniques to obtain probe diameters typically greater than 0.020 inches. Further reduction in probe diameter by such prior art methods is not attainable since the material making up the probe is highly susceptible to fracture.

Prior art attempts to manufacture ultrasonic probes having a small diameter have been less than successful. U.S. Pat. No. 5,527,273 to Manna et al. discloses a method of machining to achieve a diameter of 0.020 inches, or greater, at the distal end of the device. The Manna et al. process results in a probe having limited flexibility and the probe is not capable of producing significant cavitational energy via transverse vibrations. In addition, Manna et al. discloses manufacturing a small diameter device comprising providing a first section, a second section of different diameter, and a means to connect the first section to the second section. Although the small diameter of the distal end of the Manna et al. device allows for generation of cavitational energy, connecting a first section to a second section presents a high likelihood of fracture and an inefficient method of manufacturing the device. Thus, a need exists in the art for an ultrasonic probe having varying diameters that can be manufactured from a single metal stock.

U.S. Pat. No. 5,993,408 to Zaleski discloses a small diameter needle for cutting tissue at a distal end of the device. The Zaleski device, a thin tip phaco needle, comprises a body having a longitudinal bore for enabling passage of cut tissue therethrough. A distal end of the Zaleski device comprises a tip for cutting tissue and a proximal end for engaging a handpiece. The tip includes chamfer means for enhancing cutting efficiency of the tip. The chamfer means may be comprised of a beveled or stepped cutting edge of the tip, having a wide proximal wall and a thin distal wall, the distal wall having a cross section of about half of a cross section of the wide proximal wall. The Zaleski device is limited in that only tissue in contact with the tip of the needle is treated. Additionally, the Zaleski device is not used to create cavitational energy via transverse vibration along the length of the needle and there is no indication that the Zaleski device could be used to provide such energy. Further, the Zaleski patent does not disclose an apparatus or method of manufacturing the needle. Thus, a need exists in the art for an efficient and reliable method to manufacture small diameter ultrasonic probe.

U.S. Pat. No. 4,870,953 to DonMicheal et al. discloses an elongated, solid, flexible probe attached at one end to an ultrasonic energy source and having a rounded probe tip at a distal end, the probe tip being capable of both longitudinal and transverse motion. The DonMicheal et al. device is limited in that it does not disclose the treatment of tissue along a length of the probe and only discloses tissue treatment at the probe tip. Further, the DonMicheal et al. patent does not disclose an apparatus or method of manufacturing a small diameter medical device. Thus, a need exists in the art for an efficient and reliable method to manufacture small diameter ultrasonic probe.

Accordingly, there is a need in the art for an apparatus and method to manufacture small diameter ultrasonic probes capable of vibration in a transverse mode for incorporation in tissue ablation medical devices.

SUMMARY OF THE INVENTION

The present invention is an apparatus and method for manufacturing small diameter ultrasonic probes capable of vibrating in a transverse mode that can be used in ultrasonic tissue ablation. More particularly, the present invention provides an apparatus and method of manufacturing ultrasonic probes having a diameter at the functional end of less than 0.020 inches. The apparatus includes a die, a style puller which is used to engage a functional end of the small diameter medical device, and a die room puller which is used to draw the medical device through the die. The die includes a bell-shaped lead-in on a front side of the die and a bell-shaped lead-in on a back side of the die allowing for reversal of the direction of the draw. Reversing the draw during the drawing process allows for introduction of segments of decreasing diameter from a proximal end of the ultrasonic probe to a distal end of the probe, concluding in a functional end of diameter less than 0.020 inches.

The method of the present invention includes heat treating a large diameter medical device, drawing the large diameter device through a die and reversing the direction of the draw of the medical device through the die in order to provide a medical device having a varying diameter along a length of the method device. The method is repeated until a final diameter is reached. The method of the present invention further includes providing a plurality of dies where a subsequent die has a diameter smaller than the previous die enabling a stepwise reduction in a diameter of the medical device until reaching a final diameter of the medical device.

The present invention is an apparatus and method for manufacturing small diameter ultrasonic probes capable of vibrating in a transverse mode that can be used in ultrasonic medical devices for tissue ablation. The present invention provides an apparatus and method of manufacturing ultrasonic probes having a diameter at the functional end of less than 0.020 inches. Furthermore, the probe functions in a transverse mode along the length of the probe as disclosed in Assignee's co-pending patent applications Ser. No. 09/618,352 and Ser. No. 09/917,471, the entirety of which are hereby incorporated by reference.

The present invention provides for a method of manufacturing a small diameter ultrasonic probe including a drawing and annealing process from a precursor probe of larger diameter obtained by a conventional machining process. The method of the present invention comprises drawing the large diameter probe obtained by machining through either a single die or a series of dies decreasing stepwise in diameter thereby enabling a stepwise reduction in probe diameter to a final value. The dies used in the drawing process are constructed such that they include lead-ins on both sides of the die. The lead-ins are of a bell-shape and allow reversing the direction of the draw, or a retrograde pull that is capable of reducing the diameter of a metallic material such as a pre-machined probe that is drawn through them. Reversing the draw during the drawing process allows for introduction of segments of decreasing diameter either in a continuous or stepwise manner along the longitudinal axis of the probe from a single metal stock, thereby maintaining its integrity and mechanical strength to preclude fracturing during its operation in the medical device.

In one aspect of the present invention, the die is made from materials including, but not limited to, tungsten, stainless steel, carbide, diamond or similar materials known to those skilled in the art and is capable of reducing the diameter of the medical device sequentially by about 1% to 5% with each subsequent draw. In another aspect of the present invention, an assembly of dies are arranged serially, each die smaller than the one before, such that they provide a sequential reduction in diameter of the medical device being drawn through the assembly.

The method of the present invention for manufacturing a small diameter ultrasonic probe includes providing a medical device which has been previously machined to a diameter greater than or equal to 0.020 inches, providing the aforementioned die or die assembly including a lead-in on both sides of each die, heat treating the medical device through an annealing process and drawing the medical device through one to a plurality of dies resulting in the small diameter ultrasonic probe. The method of manufacturing of the present invention may result in the small diameter ultrasonic probe having abutting sections of decreasing diameters. The small diameter ultrasonic probe is in one aspect drawn manually and in another aspect drawn mechanically through one to a plurality of dies. Additionally, a lubricant including, but not limited to, lithium grease, soaps, oils, other greases or other similar lubricants known to those skilled in the art are used to lubricate the die assembly during the drawing process. In one aspect of the present invention, drawing the ultrasonic probe through the aforementioned die assembly provides a method for manufacturing an ultrasonic probe with a small diameter, and further provides a method to decrease the diameter of the said ultrasonic probe by about 1% to 5% with each subsequent draw. The decreased diameter of the said present invention provides increased flexibility of the probe that enables it to vibrate in a transverse mode.

A distinguishing feature of the present invention is the ability to manufacture probes of extremely small diameter (small diameter probes) compared to previously disclosed devices (large diameter probes) without loss of efficiency or efficacy, since the tissue fragmentation process in not dependent on an area of the probe tip (distal end). Highly flexible probes can therefore be obtained to mimic device shapes that enable facile insertion into highly occluded or extremely small interstices without resulting in breakage of the probe or puncture or damage of the tissue or body cavity while ensuring optimal results.

In another aspect of the present invention, the metallic object is exposed to a change in temperature through an annealing process. The annealing process is performed prior to the metallic object being drawn through a single die or intermittently while the metallic object is drawn through a succession of smaller dies. In yet another aspect of the present invention, the annealing process is performed after drawing the metallic object through a number of dies to minimize, eliminate or nullify the work hardening that will have taken place. After the metallic object is annealed at an elevated temperature and subsequently cooled to room temperature the drawing process is resumed. The change in temperature, which results from the annealing process, controls the amount work hardening and the resulting mechanical properties of the small diameter ultrasonic probe. The need for annealing and the degree of annealing will be evident to those skilled in the art. In a further aspect of the present invention, the tip of the small diameter ultrasonic probe is shaped by the process of forging, swaging, lathing, or any process of shaping metal known to those of skill in the art.

BRIEF DESCRIPTION OF THE DRAWINGS

The present invention will be further explained with reference to the attached drawings, wherein like structures are refered to by like numerals throughout the several views. The drawings are not necessarily to scale, with emphasis instead generally being placed upon illustrating the principles of the present invention.

FIG. 1 illustrates a side-view of a small diameter ultrasonic probe manufactured in accordance with the present invention.

FIG. 2 illustrates a side-view of a small diameter ultrasonic probe manufactured in accordance with the present invention.

FIG. 3 illustrates a cross-sectional view of a drawing die according to the present invention.

FIG. 4a illustrates the horizontal cross-sectional view of a style puller according to the present invention.

FIG. 4b illustrates the vertical cross-sectional view of a style puller according to the present invention.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

The present invention relates generally to the manufacture of small-diameter medical devices. More particularly, the present invention is an apparatus and method for manufacturing small diameter ultrasonic probes capable of vibrating in a transverse mode that can be used in ultrasonic medical devices for tissue ablation.

The following terms and definitions are used herein:

"Probe" as used herein refers to a device capable of being adapted to an ultrasonic generator means, which is capable of propagating the energy emitted by the ultrasonic generator means along its length, and is capable of acoustic impedance transformation of ultrasound energy to mechanical energy.

"Transverse" as used herein refers to vibration of a probe at right angles to the axis of a probe. A "transverse wave" as used herein is a wave propagated along an ultrasonic probe in which the direction of the disturbance at each point of the medium is perpendicular to the wave vector.

"Lead-in" as used herein refers to the opening at the mouth of the drawing die.

"Work hardening" as used herein refers to the increase in strength that accompanies plastic deformation of a metal.

"Small diameter" as used herein refers to an ultrasonic probe with a diameter less than 0.020 inches.

"Large diameter" as used herein refers to an ultrasonic probe with a diameter greater than or equal to 0.020 inches.

"Memory metals" as used herein refers to metals that return to their original shape if deformed.

"Piezoelectric metals" as used herein refers to as metals that relate to or involve piezoelectricity. "Piezoelectricity" as used herein refers to the generation of electricity or of electric polarity in dielectric crystals subjected to mechanical stress, or the generation of stress in such crystals subjected to an applied voltage.

"Ductile" materials as used herein refer to materials which are easily molded or shaped; or easily drawn into a wire or hammered.

The present invention provides a manufacturing apparatus and method to fabricate a small diameter ultrasonic probe capable of oscillating in a transverse mode. More particularly, the present invention provides a method of manufacturing probes having a diameter at a functional end of less than 0.020 inches.

A small diameter ultrasonic probe of the present invention is shown generally at 1 in FIG. 1. The ultrasonic probe 1 includes a probe tip 2, a functional end 4 and from one to a plurality of transforming elements 8 and 12. The transforming element 12 is larger in diameter than the transforming element 8 which is larger in diameter than the functional end 4 of the probe tip 2. Each of the transforming elements 8 and 12 are connected by connecting areas 10 which transition from one diameter to the next. The functional end 4 is connected to the transforming elements 8 and 12 by a connecting area 6. In one embodiment of the present invention as illustrated in FIG. 1, the small diameter ultrasonic probe 1 is of sufficient rigidity in order to avoid fracturing or breaking.

FIG. 2 shows another embodiment of a small diameter ultrasonic probe 1 of the present invention. The ultrasonic probe 1 includes a probe tip 2, a functional end 4 and from one to a plurality of transforming elements 8 and 12 one larger in diameter than the previous one from the probe tip 1 to the attachable end of the probe 14. As shown in FIG. 2, the attachable end of the probe in one embodiment is attached to a handle 16. Each of the transforming elements 8 and 12 are connected by a connecting area 10 which transition from one diameter to the next. The functional end 4 is connected to the transforming elements 8 and 12 by the connecting area 6. In one embodiment of the present invention as illustrated in FIG. 2 the ultrasonic probe 1 is of sufficient flexibility to cause sufficient cavitation energy to cause tissue ablation.

The ultrasonic probe 1 is made from the materials selected from the group including "memory metals", "piezoelectric materials", or any material that is "ductile" such as, for example, metals including titanium, titanium alloys or similar materials known to those skilled in the art. In one embodiment, the ultrasonic probe is made from titanium. In a further embodiment of the present invention, the ultrasonic probe functions in a transverse mode.

FIG. 3 shows a cross-sectional view of the drawing die 20 of the present invention. The drawing die 20 comprises a bell-shaped lead-in 22 on a front side 24 and a bell-shaped lead-in 23 on a back side 25 which allows for the direction of the draw to be reversed for a retrograde draw. Reversal of the direction of the draw allows the functional end 4 of the probe 1 to have a smaller diameter than those of the transforming elements 8 and 12 while being made of one contiguous piece of material to increase the strength and flexibility of the probe. The die 20 is made from the material selected from the group including, but not limited to, tungsten, stainless steel, carbide, diamond or similar materials known to those skilled in the art. In a preferred embodiment, the drawing die 20 is made from tungsten carbide encased in a stainless steel housing.

According to the present invention, the material is first machined to provide a diameter greater than or equal to 0.020 inches. In one embodiment of the present invention, the machined material is drawn through the drawing die 20 to reduce the diameter of the functional end 4 while undergoing an annealing process. The annealing process of the present invention includes exposing the machined material to a change in temperature resulting in decreasing the amount of work hardening and changing the strength of the resulting device. In another embodiment of the present invention, the machined material is drawn through a succession of drawing dies 20 to further reduce the diameter of the functional end 4 by about 1% to about 5% with each draw while undergoing an annealing process. In yet another embodiment of the present invention, the machined material is drawn through the drawing die 20 to reduce the diameter of the transforming elements 8 and 12 as well as the functional end 4 while undergoing the annealing process. In a further embodiment of the present invention, the machined material is drawn through a succession of drawing dies 20 to further reduce the diameter of the transforming elements 8 and 12 as well as the functional end 4 by about 1% to about 5% with each draw while undergoing the annealing process.

In one embodiment of the present invention, a lubricant selected from the group including, but not limited to, lithium grease, soaps, oils, other greases or similar lubricants known to those skilled in the art is used to lubricate the drawing die 20 while drawing the ultrasonic probe 1 through the die 20 or the plurality of dies 20. In a preferred embodiment, a lithium grease is used to lubricate the drawing die 20 while drawing the ultrasonic probe 1 through the die 20 or the plurality of dies 20.

In another embodiment, the ultrasonic probe 1 is drawn through a succession of the drawing dies 20 manually. In a preferred embodiment of the present invention, the ultrasonic probe 1 is drawn through the drawing die 20 mechanically using, for example, a die room puller 40 illustrated in FIG. 4b. Workers skilled in the art will recognize that any type of die room puller or similar device known to those skilled in the art can be used to mechanically draw the medical device through the die. In a most preferred embodiment, the ultrasonic probe 1 is drawn through a succession of drawing dies 20 mechanically using the die room puller 40 illustrated in FIG. 4b.

In one embodiment of the present invention (not shown), the shape of the probe tip 2 is formed by the process of forging. Forging is a manufacturing process where a material (i.e., a metal) is pressed, pounded or squeezed under great pressure into high strength parts known as forgings. The forging process is normally (but not always) performed hot by preheating the metal to a desired temperature before it is worked on. It is important to note that the forging process is entirely different from a casting (or foundry) process, as the metal used to make forged parts is never melted and poured as in the casting process. In another embodiment of the present invention, the shape of the probe tip 2 is formed by the process of lathing. The lathing process includes a machine for turning and for shaping articles of wood, metal, or other material, by causing them to revolve while acted upon by a cutting tool. In a preferred embodiment, the shape of the probe tip 2 is formed by the swaging. Rotary swaging is a process for reducing the cross-sectional area or otherwise changing the shape of bars, tubes or wires by repeated radial blows with one or more pair of opposed dies. Cold swaging can be performed at room temperature and is effective on thin-walled materials and on smaller reductions of cross sectional area. A benefit of the cold swagging process is that the cold working of the material improves the strength of the material. On the other hand, hot swaging is done at precise elevated temperatures. Heating is usually accomplished by use of induction heating equipment that allows for close control of heat input and swaging temperature. Greater reductions on heavy walled or difficult alloys are typically done utilizing the hot swaging method. Workers skilled in the art will recognize that any type of mechanical shaping process or similar process known to those skilled in the art can be used to shape the tip of the ultrasonic probe of the present invention.

In a preferred embodiment of the present invention, the diameter of the functional end 4 of the ultrasonic probe 1 is reduced to less than 0.020 inches. The smaller diameter of the ultrasonic probe 1 results in an increase in the flexibility of the probe 1.

FIG. 4a shows a top cross sectional view of a style puller 30 used to grasp the functional end 4 of the ultrasonic probe 1 and to draw the ultrasonic probe 1 through the die 20. In one embodiment, the style puller 30 includes a chuck-like grasper 32 to grasp the functional end 4 of the ultrasonic probe 1. Once securely held by the grasper 32, the functional end 4 can then be reduced down to a diameter less than 0.020 inch by drawing the medical device through the die 20 or series of dies 20. In another embodiment, the style puller 30 also comprises four screw plates 34 to attach the style puller 30 to a die room puller 40.

FIG. 4b shows a side cross sectional view of the style puller 30 engaged to a die room puller 40 used to draw the ultrasonic probe 1 through the drawing die 20. In one embodiment, the style puller 30 comprises a base 44 which is bolted to a table by two ends 42. In a further embodiment the style puller 30 includes a plurality of teeth 46 which are used in a ratcheting-like method with a handle 50 that is attached to the style puller 40 by a ratcheting screw 48. The plurality of teeth 46 are engaged by a ratcheting element 54 as the handle 50 is moved from a first position to a second position whereby the medical device is drawn through the die in a forward direction. In another embodiment the style puller 30 is bolted to the die room puller 40 by the screw plates 34. As the handle moves from a first position to a second position, the style puller 30 draws the functional end 4 of the ultrasonic probe 1 through the drawing die 20, the die 20 being attached to the die room puller 40. Drawing the ultrasonic probe 1 through the die 20 results in a decrease in the diameter of the functional end 4 of the ultrasonic probe 1. As the handle 50 returns from the second position to the first position, the direction of the draw on the functional end 4 of the ultrasonic probe 1 is reversed. Reversing the direction of the draw through the drawing die 20 is the mechanism by which the difference in diameter between the transforming elements 8 and 12 and the functional end 4 is achieved.

The ultrasonic probe manufactured by the present invention is described by Assignee's co-pending U.S. patent applications Ser. No. 09/618,352 and Ser. No. 09/917,471, the entirety of these applications are hereby incorporated by reference. The probe manufactured by the present invention may be used in conjunction with a flexible sheath assembly, such as those described in Assignee's co-pending U.S. patent application Ser. No. 09/775,908, the entirety of which is hereby incorporated by reference. Probes manufactured by the present invention may be used in medical procedures including tissue remodeling (disclosed in Assignee's co-pending U.S. patent application Ser. No. 09/917,471); removal of vascular occlusions (disclosed in Assignee's co-pending patent application Ser. No. 09/776,015 and Ser. No. 09/972,555); and treatment of genealogical diseases (disclosed in Assignee's co-pending patent application Ser. No. 00/000,000 (Atty. Docket No. 20563/2112)), the entirety of these applications are hereby incorporated by reference.

Variations, modifications, and other implementations of what is described herein will occur to those of ordinary skill in the art without departing from the spirit and scope of the present invention as claimed. Accordingly, the present invention is to be defined not by the preceding illustrative description but instead by the spirit and scope of the following claims.

What is claimed is:

1. A method of manufacturing a small diameter medical device comprising:
   heat treating a large diameter medical device through an annealing process;
   drawing the large diameter medical device through a plurality of dies where a subsequent die has a diameter smaller than a previous die, enabling a stepwise reduction in a diameter of the large diameter medical device to yield a small diameter medical device; and
   heat treating the medical device prior to drawing the medical device through each die of the plurality of dies.

2. The method of claim 1 wherein a final diameter of at least a portion of the small diameter medical device is less than 0.020 inches.

3. The method of claim 1 further comprising heat treating the small diameter medical device after drawing the medical device through the plurality of dies in order to minimize work hardening that will have taken place during drawing.

4. The method of claim 1 wherein the die includes a front lead-in on a front side of the die and a back lead-in on a back side of the die.

5. The method of claim 4 wherein the front lead-in and the back lead-in are bell shaped allowing reversal of the direction of the draw.

6. The method of claim 5 wherein the back lead-in is bell shaped allowing reversal of the direction of the draw.

7. The method of claim 5 wherein reversing the direction of the draw provides a small diameter medical device having a varying diameter along a length of the small diameter medical device.

8. The method of claim 1 wherein the small diameter medical device is a probe used for delivering ultrasonic energy in a transverse mode.

9. The method of claim 1 wherein the medical device is drawn manually through the die.

10. The method of claim 1 wherein the medical device is drawn mechanically through the die.

11. The method of claim 1 further comprising shaping a functional end of the small diameter medical device by a process of mechanical shaping.

12. The method of claim 11 wherein the functional end of the small diameter medical device is shaped by a process of swaging.

13. A method of manufacturing a small diameter medical device from a large diameter medical device comprising the steps of:
   (1) drawing the large diameter medical device through a die thereby reducing a diameter of the medical device; and
   (2) reversing the draw of the medical device through the die to provide a medical device having a varying diameter along a length of the medical device
   wherein steps 1, and 2 are repeated until the diameter of the medical device is less than 0.020 inches.

14. The method of claim 13 further comprising providing a plurality of dies where a subsequent die has a diameter smaller than the previous die enabling a stepwise reduction in a diameter of the medical device until reaching a final diameter of the medical device.

15. The method of claim 13 wherein the die is capable of reducing the diameter of the medical device by about 1% to about 5% with each draw of the medical device through the draw.

16. The method of claim 13 wherein the medical device is a probe used for delivering ultrasonic energy in a transverse mode.

17. The method of claim 13 wherein the method increases the flexibility of the medical device thereby improving the ability of the probe to vibrate in a transverse mode.

18. The method of claim 13 wherein the die comprises a front lead-in on a front side of the die and a back lead-in on a back side of the die.

19. The method of claim 18 wherein the front lead-in and the back lead-in are bell shaped allowing reversal of the direction of the draw.

20. The method of claim 18 wherein the back lead-in is bell shaped allowing reversal of the direction of the draw.

21. The method of claim 13 wherein the medical device is mechanically drawn through the die.

22. The method of claim 13 wherein a style puller is used to draw the medical device through the die.

23. The method of claim 22 further comprising a die room puller used to draw the medical device through the die.

24. The method of claim 23 wherein a the style puller comprises a chuck-like grasper which engages a functional end of the medical device and serves to draw the medical device through the die.

25. The method of claim 24 wherein the style puller further comprises a handle which when moved from a first position to a second position delivers a mechanical force to the style puller, drawing the medical device through the die.

26. The method of claim 25 wherein the style puller comprises a series of teeth which are engaged by a ratcheting element as the handle is moved from a first position to a second position whereby the medical device is drawn through the die in a forward direction.

27. The method of claim 26 wherein the the draw on the device reverses as the handle returns from the second position to the first position, thereby allowing for introduction of segments of decreasing diameter along a length of the medical device.

28. The method of claim 13 further comprising heat treating the large diameter medical device before drawing the large diameter medical device through a die.

29. The method of claim 28 wherein heat treating the large diameter medical device comprises an annealing process.

30. A method of manufacturing a small diameter medical device comprising:
- heat treating a large diameter medical device through an annealing process;
- drawing the large diameter medical device through a die having a bell-shaped front lead-in on a front side of the die and a bell-shaped back lead-in on a back side of the die; and
- reversing a direction of the draw to provide a small diameter medical device having a varying diameter along a length of the small diameter medical device.

31. The method of claim 30 wherein a final diameter of at least a portion of the small diameter medical device is less than about 0.020 inches.

32. The method of claim 30 further comprising providing a plurality of dies where a subsequent die has a diameter smaller than a previous die enabling a stepwise reduction in a diameter of the large diameter medical device until reaching a final diameter of the small diameter medical device.

33. The method of claim 32 further comprising heat treating the medical device prior to drawing the large diameter medical device through each die of the plurality of dies.

34. The method of claim 30 further comprising heat treating the small diameter medical device after drawing the medical device through the die in order to minimize work hardening that occurs during drawing.

35. The method of claim 30 wherein the small diameter medical device is a probe used for delivering ultrasonic energy in a transverse mode.

36. The method of claim 30 wherein the medical device is drawn manually through the die.

37. The method of claim 30 wherein the medical device is drawn mechanically through the die.

38. The method of claim 30 further comprising shaping a functional end of the small diameter medical device by a process of mechanical shaping.

39. The method of claim 38 wherein the functional end of the small diameter medical device is shaped by a process of swaging.

* * * * *